US012201459B2

(12) United States Patent
Moore et al.

(10) Patent No.: US 12,201,459 B2
(45) Date of Patent: Jan. 21, 2025

(54) SENSORIZED MEDICAL TRAY FOR ADVANCED TRAINING

(71) Applicant: The Penn State Research Foundation, University Park, PA (US)

(72) Inventors: Jason Z. Moore, State College, PA (US); Scarlett Miller, State College, PA (US); Dailen Brown, State College, PA (US); Haroula Tzamaras, State College, PA (US); Jessica M. González-Vargas, State College, PA (US); E. David C. Han, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 152 days.

(21) Appl. No.: 18/132,042

(22) Filed: Apr. 7, 2023

(65) Prior Publication Data

US 2023/0320806 A1 Oct. 12, 2023

Related U.S. Application Data

(60) Provisional application No. 63/329,064, filed on Apr. 8, 2022.

(51) Int. Cl.
| | |
|---|---|
| *A61B 50/33* | (2016.01) |
| *A61B 90/00* | (2016.01) |
| *G09B 19/24* | (2006.01) |
| *A61B 50/30* | (2016.01) |

(52) U.S. Cl.
CPC .............. *A61B 50/33* (2016.02); *A61B 90/36* (2016.02); *G09B 19/24* (2013.01); *A61B 2050/3015* (2016.02)

(58) Field of Classification Search
CPC . A61B 50/33; A61B 90/36; A61B 2050/3015; G09B 19/24
USPC ................................ 206/370, 557, 559, 565
See application file for complete search history.

(56) References Cited

U.S. PATENT DOCUMENTS

| | | | |
|---|---|---|---|
| 2006/0109105 A1* | 5/2006 | Varner ................... | G06Q 10/08 340/539.12 |
| 2020/0373008 A1* | 11/2020 | Nunes .................... | A61B 90/90 |
| 2022/0125543 A1* | 4/2022 | Birkbeck ............... | A61B 50/34 |
| 2022/0327962 A1* | 10/2022 | Moore .................. | G09B 23/285 |
| 2023/0146947 A1* | 5/2023 | Shelton, IV ........ | A61B 17/1285 606/144 |
| 2023/0364290 A1* | 11/2023 | Hamidi .................. | G16H 20/40 |

* cited by examiner

*Primary Examiner* — Jacob K Ackun
(74) *Attorney, Agent, or Firm* — DINSMORE & SHOHL LLP

(57) ABSTRACT

A Computer Vision enabled Smart Tray (CVST) is designed for use in medical training, such as for Central Venous Catheterization (CVC). The tray is configured to hold a plurality of medical instruments. A support surface supports the tray with areas that are selectively illuminable, and a sensing system is operable to sense the presence of instruments or supplies in at least some areas of the tray. Background color is used by the computer vision algorithm to distinguish between tools and the tray. In addition, the computer vision algorithm is evaluated for accuracy in tool detection.

19 Claims, 5 Drawing Sheets

SENSORIZED MEDICAL TRAY FOR ADVANCED TRAINING

CROSS-REFERENCE TO RELATED APPLICATION

This application claims priority to U.S. Provisional Application No. 63/329,064, filed Apr. 8, 2022, the contents of which are incorporated by reference herein in its entirety. U.S. application Ser. No. 17/716,543, filed Apr. 8, 2022, is also incorporated by reference.

GOVERNMENT SUPPORT

The present disclosure is made with government support under Grant No. HL127316 Awarded by the National Institutes of Health. The Government has certain rights in the disclosure.

TECHNICAL FIELD

Embodiments described herein generally relate to advanced training of medical procedures.

BACKGROUND

Hospitals have traditionally used the see one, do one, teach one model when training residents to perform Central Venous Catheterization (CVC), an important procedure that occurs over 5 million times a year in the United States. CVC is a common medical procedure in which a catheter is placed into a central vein of the body to provide access to the heart for the purpose of administering medication and taking measurements. With this model, medical residents are trained by performing procedures on real patients while under supervision. The procedure is often plagued with complications that affect patient health. The procedure involves 15 major steps. Medical residents are typically trained and evaluated by experts in these skills before they are permitted to perform the procedure on patients. This evaluation usually consists of a binary checklist of steps performed correctly. The sequence of steps in CVC is important, and deviation from the correct order can result in complications or failure to complete the procedure. Due to the high rate of complications, training methods often utilize manikin simulators to allow residents to practice without endangering patients, but these methods always require expert oversight which costs valuable time.

Due to the risk this method involves for patients, many medical centers have expressed a greater interest in simulation methods to allow for repetitive practice and evaluation of procedural steps before the resident performs the procedure in the clinic. Many state of the art simulators have focused training and evaluation on the haptics involved in the procedure, neglecting training on simpler steps and detailed training on the use of the medical instruments involved. Appropriate use of these tools is vital for ensuring sterile technique throughout the procedure which reduces the risk of infection, a complication that is far too common in CVC today.

SUMMARY

The present disclosure includes several aspects for the advanced training of medical procedures. Any of the several aspects may be used in any combination with any of the other aspects or with aspects already known for the training of medical procedures. Further details on aspects of the present disclosure are provided.

In one embodiment a medical training system includes a medical tray configured to hold a plurality of medical instruments, a support surface with areas that are selectively illuminable, and a sensing system operable to sense the presence of instruments or supplies in at least some areas of the tray.

In another embodiment a method of providing medical training includes providing a medical training system including a medical tray configured to hold a plurality of medical instruments, a support surface with areas that are selectively illuminable, and a sensing system operable to sense the presence of instruments or supplies in at least some areas of the tray. The method further includes positioning a medical tray on the support surface, the tray being at least partially translucent such that illumination of the support surface is visible through the tray. The method further includes illuminating an area of the tray using the support surface to provide guidance and/or feedback to a user, and sensing the presence of instruments or supplies in at least some areas of the tray, and modifying the illuminating based on the sensing.

BRIEF DESCRIPTION OF THE DRAWINGS

The following detailed description of specific embodiments of the present disclosure can be best understood when read in conjunction with the following drawings, where like structure is indicated with reference numerals and in which.

DETAILED DESCRIPTION

Embodiments of the present disclosure are directed to an automated feedback system and a computer vision enabled smart medical tray 100 which can use computer vision to evaluate the correctness of step order to track CVC tools and tool usage.

Computer Vision Enabled Smart Tray

Figure 1A:
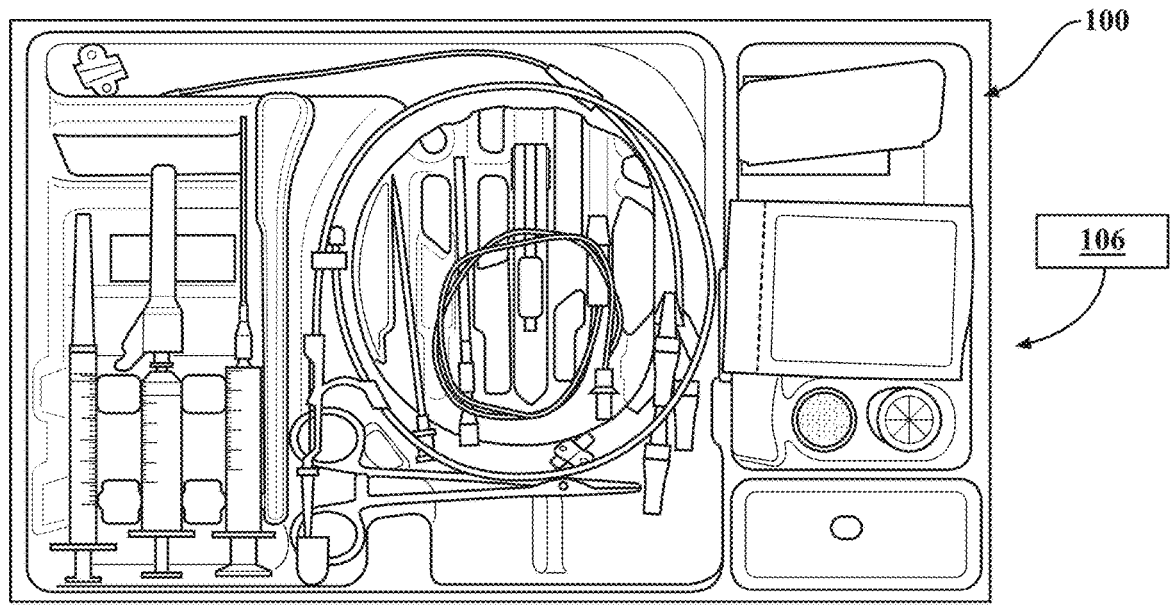
FIG. 1A depicts a CVC instrument kit.

According to one aspect of the present disclosure, a smart medical tray is provided which may be a sensorized and/or illuminated medical tray. As shown in FIG. 1A, the medical tray 100 is of the type that holds medical instruments and supplies for performing a particular procedure. Disclosed hereinbelow is tray 100 for a particular procedure, but it is understood that the present disclosure may be used with any tray for any procedure, with appropriate modifications, as will be clear to those of skill in the art. In one example, the tray 100 is formed of a material that is sufficiently translucent so as to allow illumination provided below the tray 100 to be visible to a user above the tray 100. Lighting is then provided below the tray 100 so as to provide visual feedback. As non-limiting examples, an area of the tray 100 where a particular instrument or supply is located may be illuminated in a particular color to indicate if this instrument is next to be used. Or, feedback may be provided by illuminating an area when the tool is removed, with the color of the light indicating if the tool was or was not the correct choice. As will be clear to those of skill in the art, the range of feedback or indication that may be achieved is very wide. The present disclosure is not limited to any one particular approach to feedback, but instead is directed to the broader concept of illuminating regions of the tray 100 to provide feedback. In one example, this illumination is provided using lighting elements such as used in computer displays and the semi-translucent tray 100 is positioned on the lighting elements. In this way, the illumination elements are reused and the tray 100 may be disposed of or replaced with a different tray for a different procedure. While the disclosure discusses the use of computer displays for lighting, a dedicated lighting surface may be developed using similar components.

In one embodiment, the smart medical tray 100 is a Computer Vision Enabled Smart Tray (CVST) designed for use in medical training for Central Venous Catheterization (CVC). Computer Vision (CV) is a method of image-based analysis in which an algorithm is able to detect changes in pixels from frame to frame and make conclusions about the images presented. The goal of CV is to replicate or improve upon the ability of human vision using computational systems. CV has seen significant growth due to the advent of Artificial Intelligence (AI), Deep Learning, and Neural Networks, and has applications across many industries. CV systems have been successfully used to automate the classification of diseases, medical image segmentation, cancer detection, and more. Though machine learning and AI methodologies are often used to create incredibly complex and robust CV systems, there are also many simpler methods that can be utilized effectively including color-based image recognition, template matching, and blob analysis.

The extent to which the background color of the medical tray 100 effects the ability of the computer vision (CV) algorithm to distinguish between tools and the tray 100 was investigated. In addition, the computer vision algorithm is evaluated for accuracy in tool detection. In preferred embodiments, a white monochromatic background is the most useful as a segregating background from medical tools, and the algorithm is successfully able to detect at least five different CVC tools both individually and as a group in various arrangements, even when tools overlap or touch. When the system was in error, it was nearly always due to one tool which has a color similar to that of the background. The CVST shows promise as a CVC training tool and demonstrates that computer vision can be used to accurately detect medical tools. The medical instruments can include at least a needle assembly 101, guidewire 102, scalpel 103, dilator 104, catheter 105, and disposable cup.

Figure 1B:
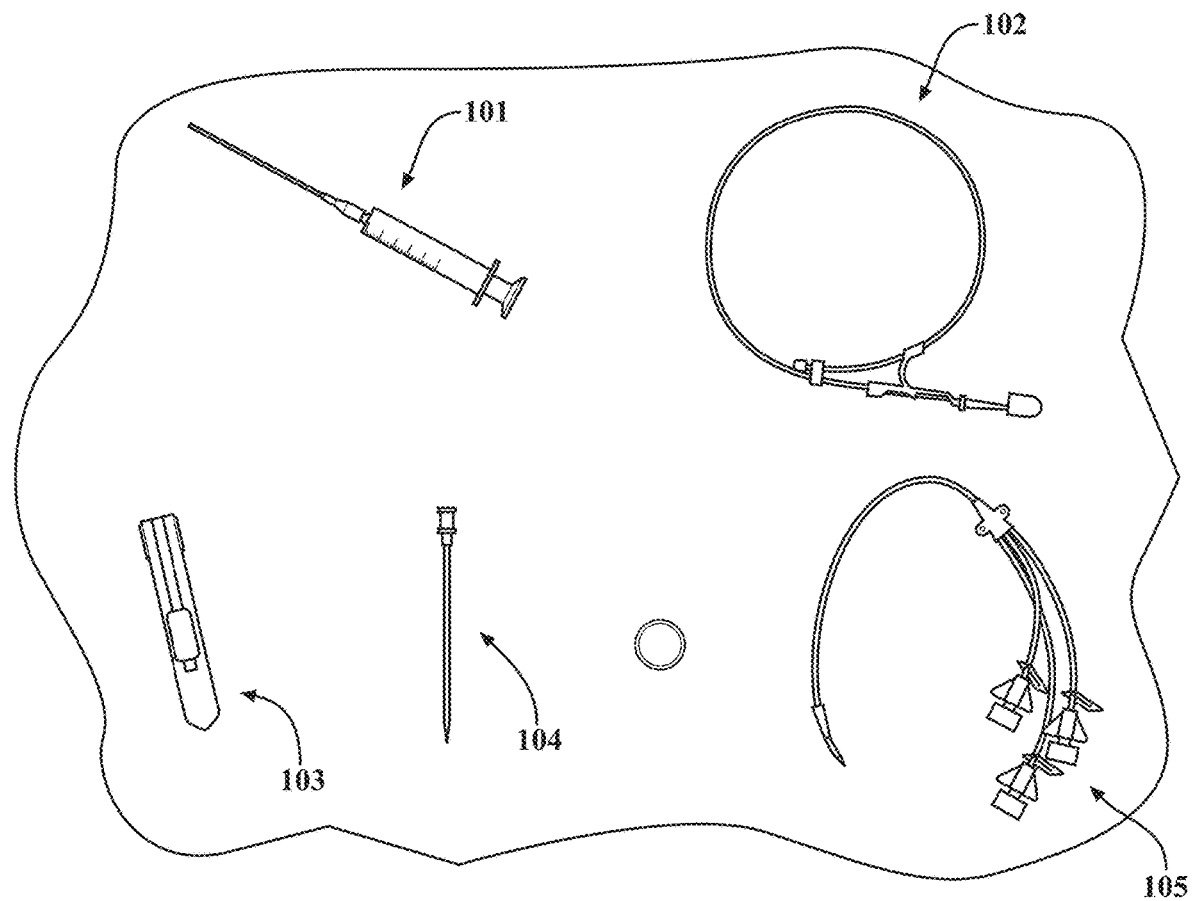
FIG. 1B depicts medical devices as images capable of processing.

As shown in FIG. 1B images of the tools, processed in MathWorks MATLAB for example, can build an algorithm capable of tracking the usage of these tools. An example of one of these sample images with the CVC tools labeled is shown in FIG. 1B.

Figure 2A:
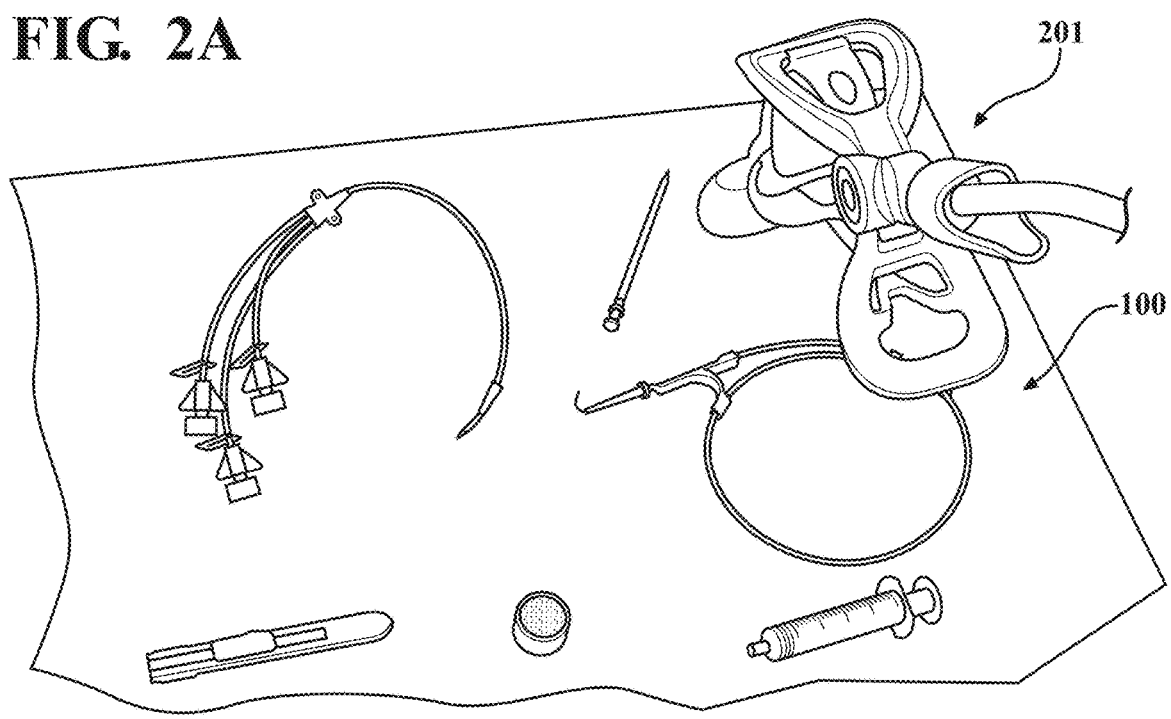
FIG. 2A depicts a medical devices tray.

As shown in FIG. 2A, the CVST system, uses a Logitech C270 HD Webcam. The CVST incorporates a tray 100 with a monochromatic background and a mounted overhead camera. A user may lay out the tools of the procedure on the tray 100 and the algorithm can detect when each tool is placed or removed from the tray 100.

The algorithm inputs an image of the tray 100 and compares the known RGB color values of the background with the color values of each pixel to determine sections of the image where the pixels deviate from the background above a certain threshold. The thresholds used are determined by calculating the average color of the background by manually selecting pixels and comparing these values. The algorithm then takes each deviated section and predicts which tool is in that section by evaluating both the size of the section and the color values that it contains.

In an embodiment, the accuracy of the system can be tested using at least five background colors to determine how contrasting colors affect the ability to accurately distinguish the tools from the background. This is by using surfaces of red, green, blue, white, and black as the tray 100 background, and adjusting thresholds manually in attempt to obtain the best possible results.

Figure 2B:
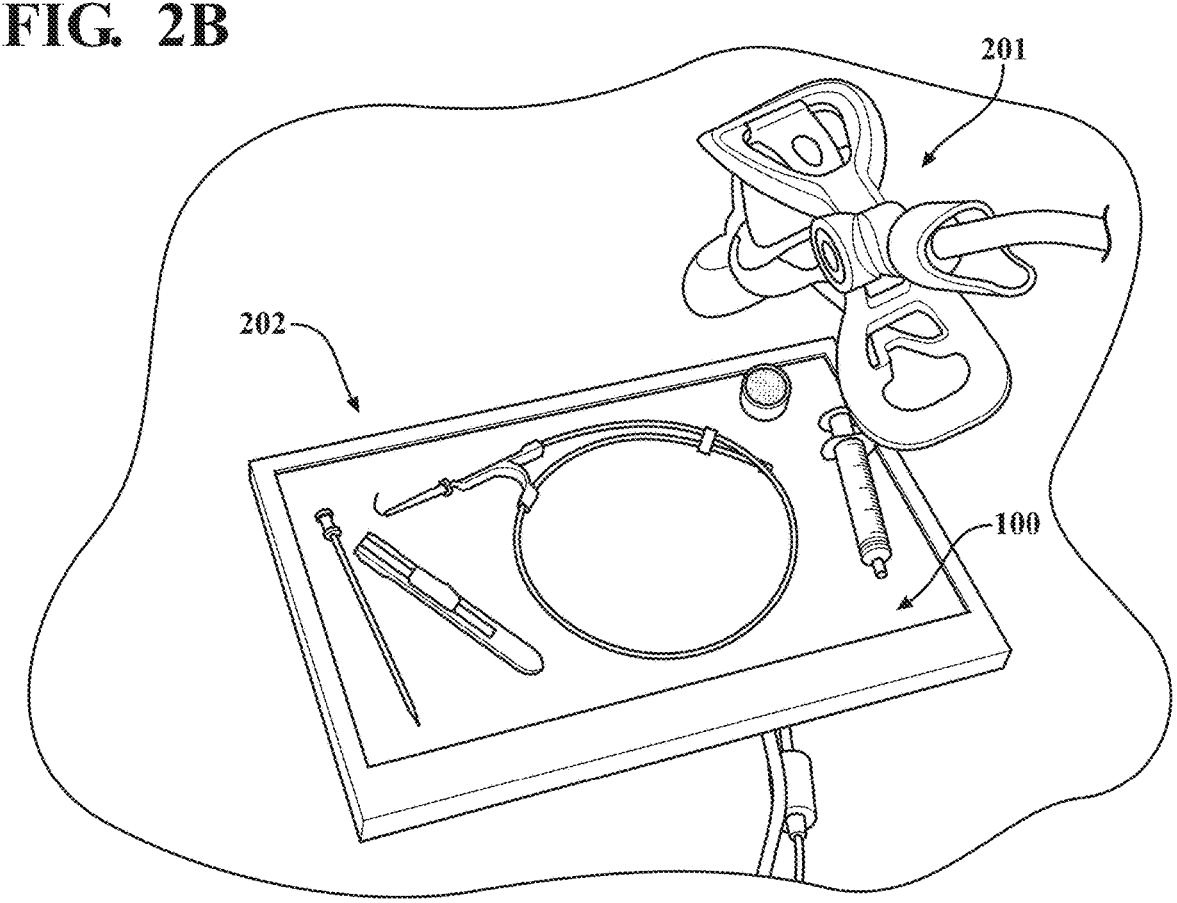
FIG. 2B depicts a medical devices tray.

In another embodiment, the accuracy of the system can be tested using a Tru-Vu SRMH display with a plain white background used as a backlight to lessen the impact of shadows, which causes notable errors in the algorithm when not backlit. The experimental setup with the backlighting display is shown in FIG. 2B. First, the tray 100 is emptied, and each of the five tools is placed and removed 10 times to determine the accuracy of the system in detecting each tool correctly. During this test, the position and orientation of the tool is randomly changed in order to test the robustness of the system. Second, all five tools are placed on the tray 100 together and each of the tools are randomly rearranged or removed 10 times to assess system accuracy when multiple tools are involved. It is important to note that the catheter 105 was excluded from this experiment due to the small size of the screen.

Figure 3:
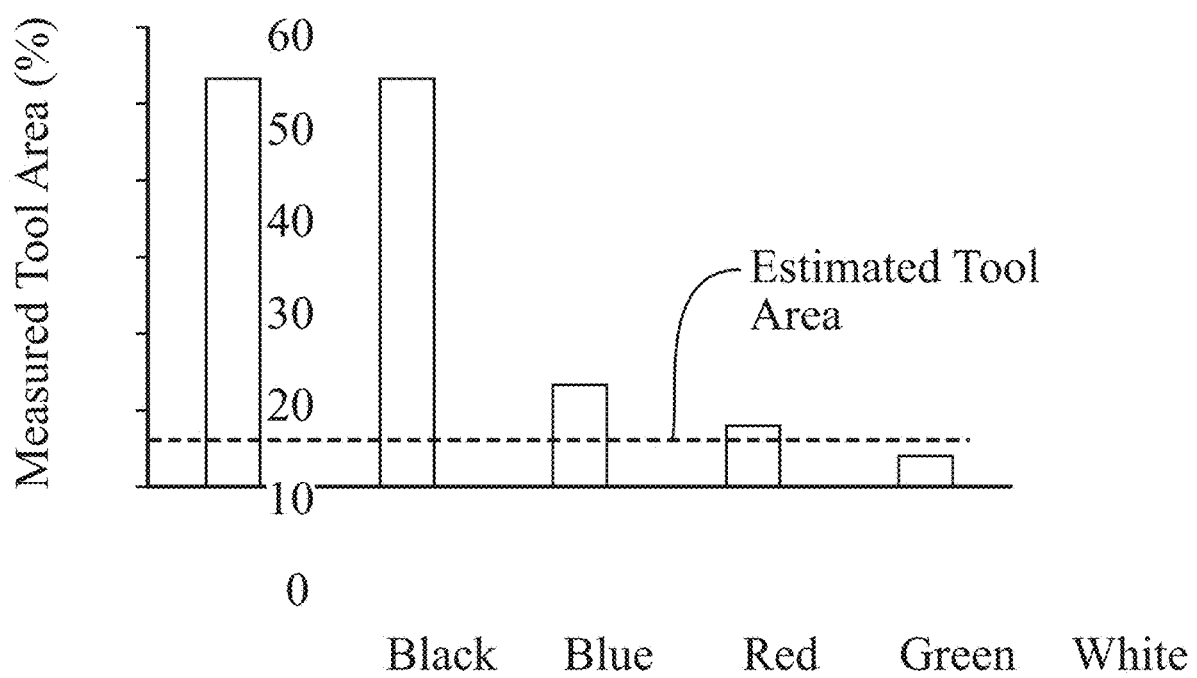
FIG. 3 depicts a graph of the percent of image detected as tools.
Figure 4:
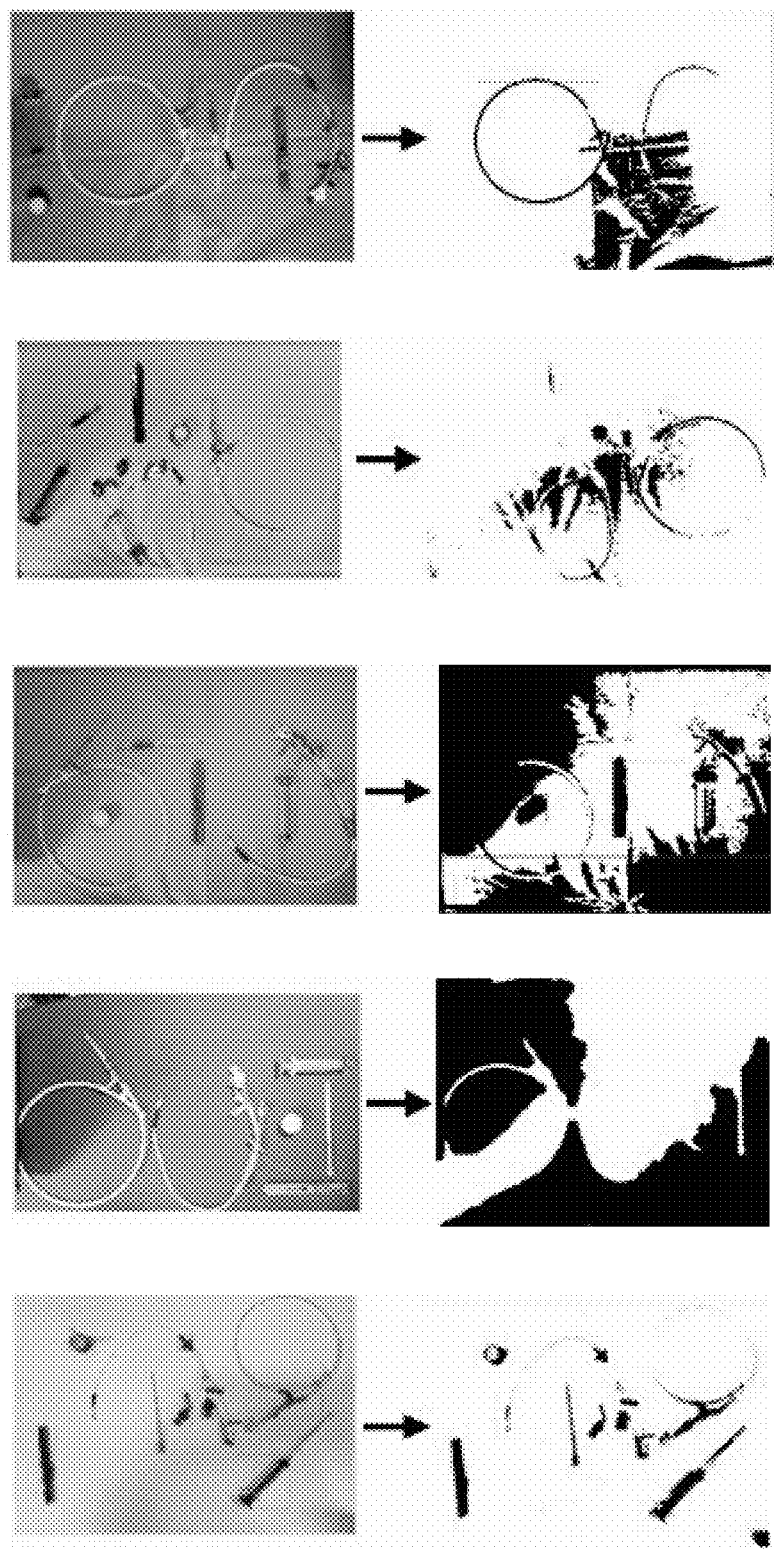
FIG. 4 depicts the effects of background color on tool detection.

FIG. 3 shows the percent area of the image that was detected as tools on the tray 100 for five different background colors. Based on a manual pixel count performed in Adobe Photoshop, less than 7% of the image will be tools and the remainder will be background. Only the white background resulted in a detection of less than 7% of the image area as tools, with the green background resulting in 7.9% and all other colors resulting in greater than 10% tool area. FIG. 4 shows an example of the results of changing the background color of the tray 100 as black and white images representing either background or tool. In this figure, each plot displays pixels as white if they are detected as background area, and as black if detected as a tool.

As seen in FIG. 4, the background color that produces the least error in distinguishing objects from the background is white. The red and green backgrounds allowed the system to more easily detect the thin tubing of the catheter 105 and guidewire 102, but caused more objects to be confused as part of the background, while the blue and black backgrounds caused the system to confuse more background area as tools. The white background suffered from similar issues caused by shadowing, but the thresholds are able to be adjusted to clearly segregate the background and tool. Adjustments to the thresholds for other background colors prove more difficult and often result in overestimation or underestimation of what areas of the image consisted of tools. As a result, in preferred embodiments, the CVST utilizes a white background.

In embodiments utilizing the backlit tray 100, the system can correctly detect the placement of the needle assembly 101, guidewire 102, and sharp's disposal cup 100% of the time. The scalpel 103 and the dilator 104 are correctly detected 70% of the time and 90% of the time respectively. It was observed that the scalpel 103 is only incorrectly detected when placed in an unnatural way, balancing on its edge, or when placed very close to the edge of the tray 100. The removal of each tool was only in error when the system didn't detect the placement of the tool previously. In addition, when all of the tools are placed on the tray 100 together, the system accurately detected the needle assembly 101, guidewire 102, and scalpel 103 100% of the time, while the dilator 104 was correctly detected 90% of the time. The sharp's disposal cup, however, was only detected 60% of the time. This is likely caused by the high amount of white on the disposal cup, which may have caused the cup edges to be confused as a part of another tool close by. This could explain why the system was able to detect the cup with perfect accuracy when placed alone, while unable to do so when placed with other tools. In multiple cases, the system was able to detect the other four tools correctly even when they overlap or touch.

This CV algorithm was able to track the location of CVC medical tools with satisfying accuracy. Through the use of more complex and robust algorithms, the CVST can be effective for CVC training, and its design can be used to create training systems for other medical procedures or tool tracking systems.

The CV algorithm can consider tool overlap, increase the tray 100 area, and apply CV to an advanced testing surface (ATS) which allows for tool interaction with simulated tissue. This complete system will allow for effective automated training of user tool interaction in CVC.

There may further be communication between the tray 100 and a surface 202, supporting the tray 100, to determine an identity of the tray 100 and therefore what training procedure is to be used. For example, the tray 100 may include a chip that is readable by the surface 202. A display surface 202 may also guide proper positioning of the tray 100, such as providing indicators for the corners of the tray 100, or sensors (not shown) may be provided for sensing the position of the tray 100 such that the location of illumination is appropriately adjusted to align with the areas of the tray 100 to be illuminated.

As a further aspect of the tray 100, the tray 100 may include sensors to determine if and when a tool or supply is positioned in the appropriate location. The sensing approach may make use of any sensing technology, as long as the technology allows the training system to determine if a tool or supply recess is filled. For example, reed switches 106 may be provided in some or all recesses of a tray 100. It may not be required to sense all locations. In a further example, the sensing technology may determine the presence and identify of the tool or supply, to determine not only if the recess is filled but if the correct tool or supply was placed in the recess.

The sensing aspect and illumination aspects are highly useful in combination, as they allow a training system to determine if a tool or supply is removed from or replaced into the tray 100 and to provide illumination for guidance and/or feedback. Further details are provided in the materials hereinbelow.

In a further embodiment, a computer vision system is provided and used to identify and track the position of individual tools in and from a tray 100. Backlighting may be provided to improve identification. The computer vision system may be combined with the lighting and/or sensing approaches discussed above.

Figure 5:
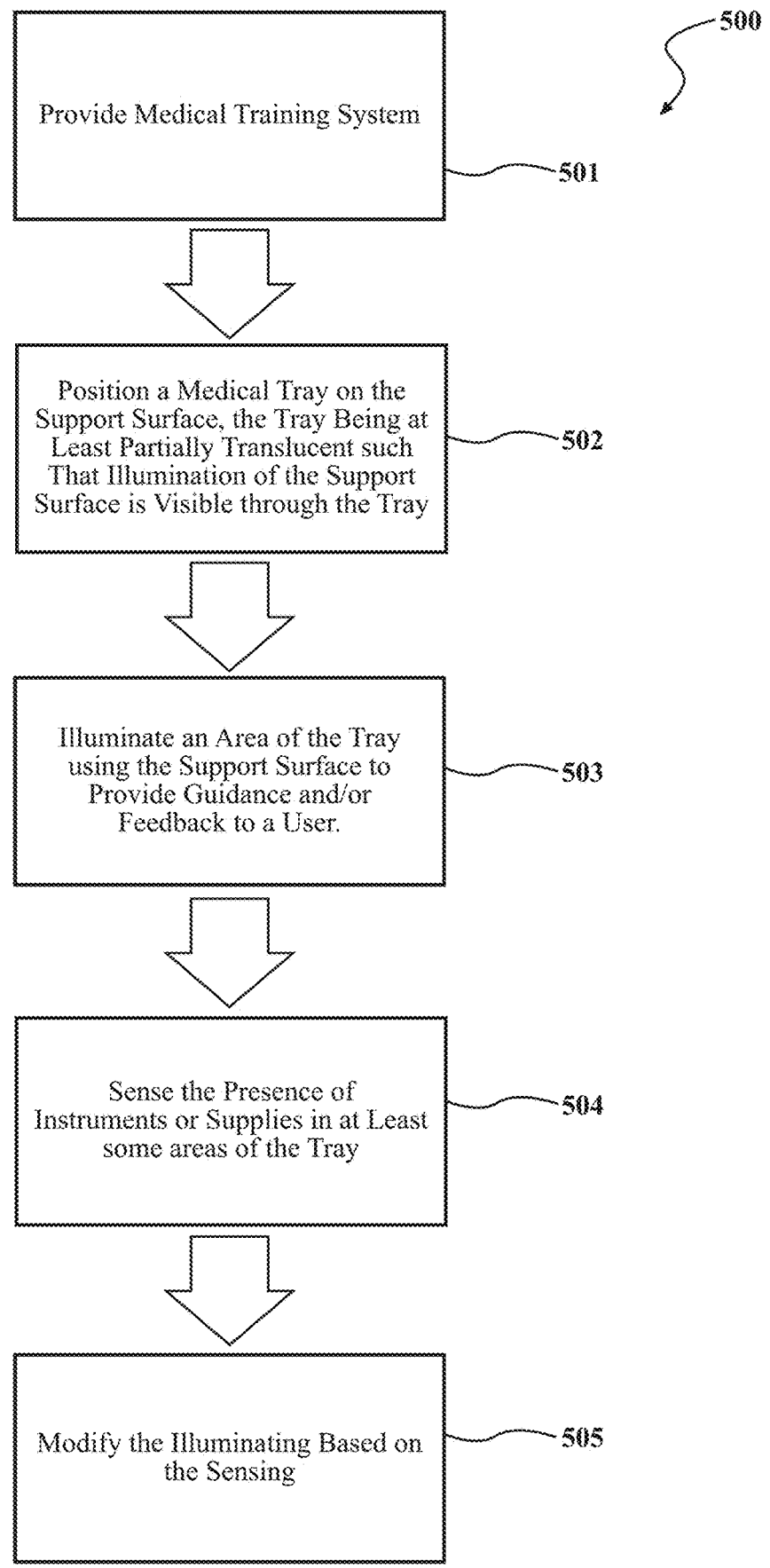
FIG. 5 is a flowchart for use of the medical devices tray.

FIG. 5 shows a flowchart of method 500. In embodiments a method of providing medical training, starts with providing a medical training system including a medical tray (e.g., tray 100), a support surface (e.g., surface 202), and a sensing system. Block 502 includes positioning the medical tray on the support surface, the tray being at least partially translucent such that illumination of the support surface is visible through the tray. Block 503 includes illuminating an area of the tray using the support surface to provide guidance and/or feedback to a user. Block 504 includes sensing the presence of instruments or supplies in at least some areas of the tray. Block 505 includes modifying the illuminating based on the sensing.

The CV algorithm tracks the usage of important CVC tools during resident training and to evaluate the accuracy of this algorithm in detecting these tools. Multiple sensors can be embedded into the tray 100 to increase usability and gather information. For example, areas of the tray 100, holding specific instruments, can be illuminated based on if the correct instrument is removed from tray 100. The tray 100 may illuminate with a first color if the correct instrument is chosen and a second color if the wrong instrument is chosen. Areas of the tray 100, holding specific instruments, can also be illuminated in the order in which the instruments are to be used. Tray 100 may sense that a certain instrument has been removed from the tray 100 and illuminate the next instrument to be used/removed.

What is claimed is:

1. A medical training system, the system comprising:
    a medical tray configured to hold a plurality of medical instruments;
    a support surface with areas that are selectively illuminable; and
    a sensing system operable to sense the presence of instruments or supplies in at least some areas of the tray.

2. The medical training system of claim 1, further comprising reed switches disposed in a plurality of recesses of the tray.

3. The medical training system of claim 1 wherein the medical tray is formed of a translucent material such that illumination provided below the tray is visible to a user above the tray.

4. The medical training system of claim 1 wherein the background color of the medical tray is a white monochromatic background.

5. The medical training system of claim 1, wherein the plurality of medical instruments includes at least a needle assembly with an introducer needle, guidewire, scalpel, dilator, catheter, and disposable cup.

6. The medical training system of claim 1, wherein the introducer needle and the scalpel are blunted.

7. The medical training system of claim 1, wherein the sensing system is a computer vision algorithm capable of distinguishing between instruments and the tray.

8. A method of providing medical training, comprising:
    providing a system comprising:
        a medical tray configured to hold a plurality of medical instruments;
        a support surface with areas that are selectively illuminable; and
        a sensing system operable to sense the presence of instruments or supplies in at least some areas of the tray;
    positioning a medical tray on the support surface, the tray being at least partially translucent such that illumination of the support surface is visible through the tray;
    illuminating an area of the tray using the support surface to provide guidance and/or feedback to a user;
    sensing the presence of instruments or supplies in at least some areas of the tray; and
    modifying the illuminating based on the sensing.

9. The method of claim 8, further comprising disposing reed switches in a plurality of recesses of the tray.

10. The method of claim 8, wherein the medical tray is formed of a translucent material such that illumination provided below the tray is visible to a user above the tray.

11. The method of claim 8, wherein the background color of the medical tray is a white monochromatic background.

12. The method of claim 8, wherein the plurality of medical instruments includes at least a needle assembly with an introducer needle, guidewire, scalpel, dilator, catheter, and disposable cup.

13. The method of claim 12, wherein the introducer needle and the scalpel are blunted.

14. The method of claim 8, wherein the sensing system is a computer vision algorithm capable of distinguishing between instruments and the tray.

15. The method of claim 14, further comprising evaluating the computer vision algorithm for accuracy in tool detection.

16. The method of claim 8, wherein modifying the illuminating based on sensing comprises illuminating areas of the tray, holding specific instruments, based on if the correct instrument is removed from tray.

17. The method of claim 16, wherein the tray illuminates with a first color if a correct instrument is chosen and a second color if an incorrect instrument is chosen.

18. The method of claim 8, wherein modifying the illuminating based on sensing comprises illuminating areas of the tray, holding specific instruments, in an order in which the instruments are to be used.

19. The method of claim 18, wherein modifying the illuminating based on sensing comprises:
   sensing that a certain instrument has been removed from the tray; and
   illuminating a next instrument to be removed.

* * * * *